Patent Number: 4,845,221
Date of Patent: Jul. 4, 1989

[54] SEROTONERGIC SUBSTITUTED PIPERAZINYL TETRALINS

[75] Inventors: Gary P. Stack, Merion; Edward J. Podlesny, New Tropoli, both of Pa.

[73] Assignee: American Home Products Corporation, New York, N.Y.

[21] Appl. No.: 181,842

[22] Filed: Apr. 15, 1988

[51] Int. Cl.⁴ .................. C07D 403/02; C07D 295/04
[52] U.S. Cl. ..................................... 544/295; 544/357; 544/392; 544/393
[58] Field of Search ...................... 544/295, 392, 393

[56] References Cited

U.S. PATENT DOCUMENTS

| | | | |
|---|---|---|---|
| 4,018,773 | 4/1977 | Condon et al. | 544/392 |
| 4,081,444 | 3/1978 | Condon et al. | 544/392 |
| 4,308,266 | 12/1981 | Seiler | 544/392 |

FOREIGN PATENT DOCUMENTS 0000395 1/1979 European Pat. Off. .
8103491 12/1981 PCT Int'l Appl. .

OTHER PUBLICATIONS

Sandoz, Inc. Chem. Abst. 90-204143s.
Smith et al., Chem. Abst. 105-78960u.
Derwent Abstract No. 37505S-B, Netherlands, Pat. No. 7,017,031, 11/69; N-(Heterozryl)Piperazinylalkyl Derivs.
Derwent Abstract No. 85-000957/01, DE 3,321,969-12/84-New 1-pyrimidyl-4-Subst. piperazine derivs. with CNS e.g. anxiolytic and antidepressant activities.
Derwent Abstract No. 85-250735/41, U.S. Pat. No. 4,640.922-3/87; N-Alkoxy:carbonyl-5-alkoxy:carbonyl di:hydro:pyrimidine cpds. useful in treating cardiovascular disorders, e.g. as hypotensives.

Primary Examiner—Donald G. Daus
Assistant Examiner—Cecilia Shen
Attorney, Agent, or Firm—Richard K. Jackson

[57] ABSTRACT

The compounds

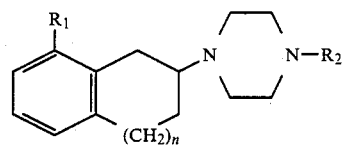

in which $R_1$ is hydroxy, alkoxy of 1 to 6 carbon atoms, amino, alkylamino of 1 to 6 carbon atoms, dialkylamino where each alkyl substituent contains 1 to 6 carbon atoms, or alkanoylamino of 2 to 6 carbon atoms;

$R_2$ is 3-trifluoromethylphenyl, 3-halophenyl, 2-pyrimidinyl, halopyrimidin-2-yl, 2-pyrazinyl or halopyrazin-2-yl; and n is one of the integers 1 or 2;

or a pharmaceutically acceptable salt thereof, are selective serotonergic agents useful in the treatment of depression and/or anxiety, as well as related sexual dysfunctions and appetite disorders.

6 Claims, No Drawings

SEROTONERGIC SUBSTITUTED PIPERAZINYL TETRALINS

BACKGROUND OF THE INVENTION

European Patent Application No. 395 discloses a group of 2-(1-piperazinyl)-tetralin derivatives which are dopamine receptor stimulants (agonists) useful as antihypertensive agents. The compounds preferred by the patentee are those in which an alkoxy or hydroxy substituent is present in 6-position of the tetralin moiety and a 2-methyl- or 2-methoxy-phenyl group or an acyloxy or acylthio group appears in 4-position of the piperazine ring (page 3,line 15 - page 4, line 4).

Derwent Abstract No. 37505S-B of Netherlands, Pat. No. 7,017,031 discloses 8-(heteroarylpiperazinylalkyl)-8-azaspiro[4,5]decane-7,9-diones as tranquilizers.

Derwent Abstract No. 85-250735/41 of U.S. Pat. No. 4,640,921 discloses the use of the same compounds as are disclosed in the preceding paragraph for the treatment of sexual dysfunction.

Derwent Abstract No. 85-000097/01 of DE 3,321,969 discloses 1-pyrimidyl-4-substituted piperazine derivatives which possess anxiolytic and antidepressant properties.

PCT application WO 81/03491 published Dec. 10, 1981 discloses compounds of the formula:

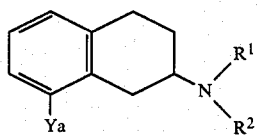

where
Ya is alkoxy, hydroxy, amino, acyloxy or acylamido;
$R^1$ is alkyl or arylalkyl;
$R^2$ is hydrogen or alkyl and $R^1$ taken with $R^2$ may be alkylene or 4 to 6 carbon atoms;
which are disclosed to be 5-HT receptor agonists with high selectivity for the 5-HT receptor over dopamine and noradrenaline receptors. These compounds are indicated to be useful in treatment of CNS disorders such as depression and sexual disturbances.

Middlemiss et al., European J. of Pharmacol. 90 151 (1983) disclose the selective 5-$HT_{1A}$ (a serotonin receptor subtype) agonist activity of 8-hydroxy-2-(di-n-propylamino)-tetralin(8-OH-DPAT).

DESCRIPTION OF THE INVENTION

In accordance with this invention, there is provided a group of 4-aryl and heteroaryl piperazinyltetralins as selective 5-$HT_{1A}$ serotonergic agents with low relative dopaminergic properties useful as antidepressant/anxiolytic agents. The compounds of this invention possess the following structural formula features:

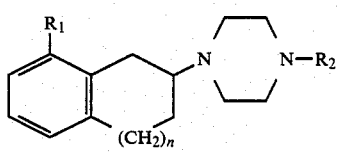

in which
$R_1$ is hydroxy, alkoxy of 1 to 6 carbon atoms, amino, alkylamino of 1 to 6 carbon atoms, dialkylamino where each alkyl substituent contains 1 to 6 carbon atoms, or alkanoyl amino of 2 to 6 carbon atoms;
$R_2$ is 3-trifluoromethylphenyl, 3-halophenyl, 2-pyrimidinyl, halopyrimidin-2-yl, 2-pyrazinyl or halopyrazine-2-yl; and
n is one of the integers 1 or 2;
or a pharmaceutically acceptable salt thereof.

Preferred among the compounds depicted above are those in which $R_1$ is hydroxy or methoxy and $R_2$ is 3-trifluoromethylphenyl, 3-halophenyl or 2-pyrimidinyl. The halo substituents may be chloro, bromo or fluoro, preferably chloro, and the aliphatic portion of the alkoxy, alkylamino, dialkylamino and alkanoylamino substituents are preferably methyl, ethyl, propyl, isopropyl, butyl, isobutyl or tertiary butyl. The variable n is preferably 1.

The pharmaceutically acceptable salts of the compounds of this invention are derived by conventional means from such acids as hydrochloric, hydrobromic, sulfuric, phosphoric, nitric, methanesulfonic, p-toluenesulfonic, acetic, citric, maleic, succinic, malonic acid and the like.

The compounds of the invention may be prepared by a variety of synthetic routes using conventional methods. For example, a

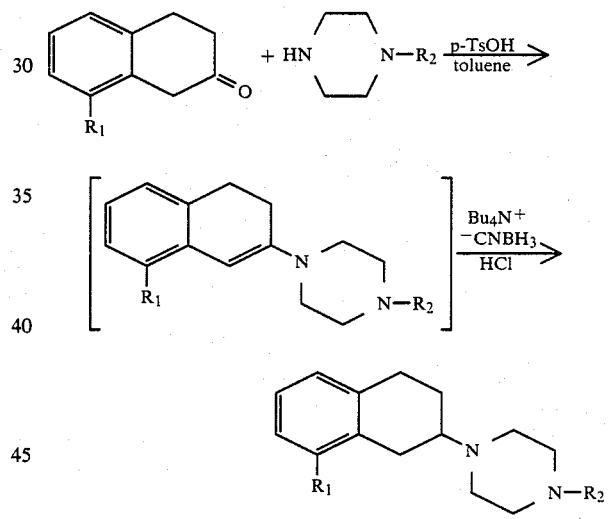

suitably substituted tetralone may be combined with the desired aryl- or heteroarylpiperazine and a trace of p-toluenesulfonic acid in a high boiling solvent such as toluene or xylene and refluxed for an extended period with water removal via a Dean-Stark trap. The intermediate eneamine may then be treated without isolation with a suitable reducing agent such as tetra-n-butyl ammonium cyanoborohydride in the presence of hydrochloric acid.

An analogous preparation involves the reaction of piperazine with the desired tetralone followed by reduction as above and N-substitution with

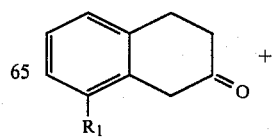

-continued

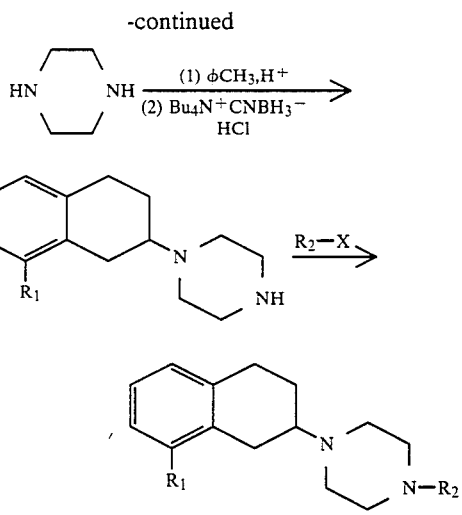

the desired aryl or heteroaryl halide.

Similarly, a suitably substituted amino tetralin may be alkylated with the appropriate bis-2-haloethylaminoarene or heteroarene under the

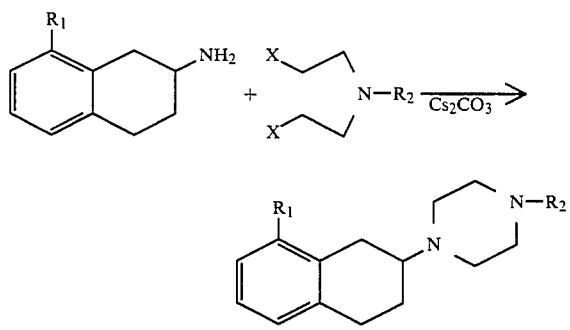

influence of a suitable base such as cesium carbonate.

The following examples illustrate, without limitation, the preparation of representative compounds of the invention.

EXAMPLE 1

1-(1,2,3,4-tetrahydro-8-methoxy-2-naphthalenyl)-4-[3-(trifluoromethyl) phenyl]piperazine 8-Methoxy-2-tetralone (3.7 g, 21 mmole), 1-($\alpha,\alpha,\alpha$-trifluoro-m-tolyl)piperazine (4.9 g, 21 mmole) and 0.4 g of p-toluenesulfonic acid were dissolved in 200 ml of toluene and refluxed for three days with water removal via a Dean-Stark trap. Upon cooling, 10.5 ml of 4 N isopropanolic HCl was added following portionwise by 5.93 g (21 mmole) of tetra-n-butyl ammonium cyanoborohydride. The mixture was heated at reflux for one hour, cooled and the solvent removed in vacuo. The product was redissolved in chloroform, washed with saturated $NaHCO_3$ solution and saturated brine, dried over $MgSO_4$, filtered and concentrated in vacuum. The resulting residue was column chromatographed on 75 g of silica gel with chloroform as the eluent. The crude title compound was crystallized from isopropanol with the addition of 4 N isopropanolic HCl to give 2.02 g of the monohydrochloride, m.p. 250°–253° C.

Elemental analysis for $C_{22}H_{25}F_3N_2O \cdot HCl$.
Calc'd: C, 61.89; H, 6.14; N, 6.56.
Found: C, 61.89; H, 5.93; N, 6.60.

EXAMPLE 2

2-[4-(1,2,3,4-tetrahydro-8-methoxy-2-naphthalenyl)-1-piperazinyl]pyrimidine

8-Methoxy-2-tetralone (3.5 g, 20 mmole), 1-(2-pyrimidinyl) piperazine dihydrochloride (4.6 g, 20 mmole), 0.38 g of p-toluenesulfonic acid and 3.48 ml of diisopropylethylamine were combined in 200 ml of toluene and the mixture refluxed under $N_2$ for three days with water removal via a Dean-Stark trap. After the reaction had cooled, 10.5 ml of 4 N isopropanolic HCl was added, followed in portions by 5.93 g of tetra-n-butyl ammonium cyanoborohydride. The mixture was refluxed under $N_2$ for one hour and the solvent removed in vacuum. The residue was redissolved in 300 ml of $CHCl_3$, washed with saturated $NaHCO_3$ solution, dried over $MgSO_4$, filtered, and evaporated in vacuum. The crude product was column chromatographed on 75 g of silica gel employing chloroform as the eluent and the relevant fractions were combined and concentrated in vacuum. The crude title compound was crystallized from 50 ml of isopropanol with addition of 4 N isopropanolic HCl to obtain 2.0 g of the title compound as the monohydrochloride. A second crystallization from isopropanol gave 1.3 g of monohydrochloride, m.p. 273°–276° C. (d).

Elemental analysis for $C_{19}H_{24}N_4O \cdot HCl$.
Calc'd: C, 63.23; H, 6.98; N, 15.53.
Found: C, 62.99; H, 6.97; N, 15.25.

EXAMPLE 3

1-(1,2,3,4-tetrahydro-8-hydroxy-2-naphthalenyl)-4-[3-(trifluromethyl) phenyl]piperazine 1-(1,2,3,4-Tetrahydro-8-methoxy-2-naphthalenyl)-4-[3-(trifluromethyl)phenyl]piperazine hydrochloride (2.7 g, 6.0 mmole) was dissolved in 125 ml of methylene chloride and cooled to $-78°$ C. in a dry ice/acetone bath. To the cold solution was added a mixture of 18.9 ml of 1 M boron tribromide and 25 ml of methylene chloride. The reaction was allowed to come to room temperature and stirred for three days. The reaction was quenched with methanol and concentrated in vacuo. The residue was column chromatographed on 100 g of silica gel with 5% methanol/chloroform as eluent and the crude title compound thus obtained was crystallized first from isopropanol with addition of 4 N isopropanolic HCl and then from acetone to yield 1.2 g of the title compound as the monohydrochloride, m.p. 207°–209° C.

Elemental analysis for $C_{21}H_{23}N_2OF_3 \cdot HCl$.
Calc'd: C, 61.09; H, 5.86; N, 6.77.
Found: C, 61.13; H, 5.80; N, 6.87.

EXAMPLE 4

2-[4-(1,2,3,4-tetrahydro-8-hydroxy-2-naphthalenyl)-1-piperazinyl]pyrimidine 2-(4-(1,2,3,4-Tetrahydro-8-methoxy-2-naphthalenyl)-1-piperazinyl]-pyrimidine hydrochloride (1.62 g, 5.0 mmole) was dissolved in 185 ml of methylene chloride and cooled to $-78°$ C. in a dry ice/acetone bath. A mixture of 15 ml of 1 M boron tribromide and 15 ml of methylene chloride was added. The reaction mixture was allowed to come to room temperature and it was then stirred for three days. The reaction was then poured into a saturated $NaHCO_3$ solution and the product extracted with 600 ml of chloroform. This solution was dried over MgSO$_4$, filtered, and concentrated in vacuum. The residue was column chromatographed on 100 g of silica gel with 5% methanol/chloroform and the crude title compound thus obtained was crystallized from isopropanol with addition of 4 N isopropanolic HCl and recrystallized from acetone to give 1.1 g of the title compound as the hydrochloride, monohydrate, m.p. >300° C.

Elemental analysis for $C_{18}H_{22}N_4O·HCl·H_2O$.
Calc'd: C, 59.24; H, 6.91; N, 15.36.
Found: C, 58.88; H, 6.37; N, 15.07.

The relatively low D-2 dopamine receptor affinity of the compounds of this invention was established by a modification of the procedure of Fields et al., *Brain Res.*, 136, pp. 578–584 (1977) and Yamamura et al., eds. Neurotransmitter Receptor Binding, Raven Press, N.Y. (1978), wherein homogenized limbic brain tissue is incubated with $^3$H-spiroperidol and various concentrations of test compound, filtered, washed and shaken with Hydrofluor scintillation cocktail (National Diagnostics) and counted in a Packard 460 CD scintillation counter.

The serotonergic properties of the compounds of this invention were established by standard pharmacologically accepted procedures involving the measurement of the compound's ability to displace [$^3$H]8-OH DPAT (dipropylaminotetralin) from the 5-HT-1A serotonin receptor by the procedure of Hall et al., *J. Neurochem.* 44: 1685-1696, 1985. Compounds of this invention, like the anxiolytic buspirone, exhibit potent affinity for this receptor subtype.

The compounds of the invention were thereby shown to have potent affinity for the 5-HT-1A serotonin receptor with little or no affinity for D-2 dopamine receptors. As such they are useful for the treatment of CNS disorders such as depression, anxiety, sexual dysfunction, and related disorders, with a very low liability for extrapyramidal side effects and tardive dyskinesia.

The experimental results obtained by the standard test procedures employed catagorize the compounds of this invention as possessing quite unique, selective, serotonergic properties when compared with very closely related structural analogues. To illustrate this fact, the following table of data is presented. The first four compounds are specifically exemplified in this application. Their activity profile demonstrates very high 5-HT receptor binding properties in relation to low dopamine receptor binding properties, compound number 1 being exemplary with 97% inhibition of 8-OH DPAT and 5% inhibition of spiroperidol. With these compounds, the most selective serotonin receptor binding is observed with a electron donating group in 8-position and the heteroaryl 2-pyrimidine on the piperazin-4-yl nitrogen (compound 4). That selective activity is most closely approximated in the N-phenyl piperazine analogues when an electron withdrawing group, such as the trifluoromethyl substituent, is placed in meta position of the phenyl ring. Placement of an electron donating group (methoxy) in ortho position of the phenyl ring (compound 5) reverses the selective activity with almost complete loss of serotonin receptor agonism and relatively high dopamine receptor binding. Shifting the electron donating group from 8-position of tetralin to 7-position (compound 6) affords reduced 5-HT$_{1A}$ agonism with relative high dopamine receptor binding (unacceptable separation of properties) in the m-trifluoromethylphenyl series, higher D-2 binding in the ortho-methoxy-phenyl series (compound 7) and improved separation of properties with emphasis on 5-HT$_{1A}$ binding in the 2-pyrimidine series (compound 8). Shifting the methoxy group to 6-position of tetralin increased D-2 binding markedly in the m-trifluoromethylphenyl series (compound 9) which property was retained in the 6-hydroxy tetralin analogue (compound 10). A marked reduction in 5-HT$_{1A}$ binding was observed in the 6-methoxy, 2-pyrimidine series (compound 11), which drop off to negligible activity in the 6-hydroxy analogue (compound 12) which also demonstrates negligible D-2 binding.

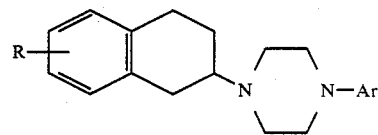

| | R | Ar | % Inhibition 1 μM D-2 | % Inhibition 1 μm (Ki nM) 5 HT$_{1A}$ |
|---|---|---|---|---|
| 1 | 8-OCH$_3$ | m-CF$_3$ phenyl | 5% | 97% (11) |
| 2 | 8-OH | m-CF$_3$ phenyl | 46% | 100% (14) |
| 3 | 8-OCH$_3$ | 2-pyrimidine | 3% | 84.6% (63 nM) |
| 4 | 8-OH | 2-pyrimidine | 0% | 91% (109) |
| 5 | 8-OCH$_3$ | o-methoxy phenyl | 72% | 4% |
| 6 | 7-OCH$_3$ | m-CF$_3$ phenyl | 49% | 77% |
| 7 | 7-OCH$_3$ | o-CH$_3$O phenyl | 65% | 93% |
| 8 | 7-OCH$_3$ | 2-pyrimidine | 11% | 83% |
| 9 | 6-OCH$_3$ | m-CF$_3$ phenyl | 65% | 97% |
| 10 | 6-OH | m-CF$_3$ phenyl | 72% | 87% |
| 11 | 6-OCH$_3$ | 2-pyrimidine | | 44% |
| 12 | 6-OH | 2-pyrimidine | 7% | 15% |

The results of these experiments demonstrate the marked selectivity of the compounds of this invention for the serotonin 5-HT$_{1A}$ receptor subtype as opposed to the dopamine D-2 receptor. This pharmacological profile resembles that of the known anxiolytics buspirone, gepirone and ipsapirone and the antidepressant 8-OH DPAT, which also show selective 5-HT$_{1A}$ serotonin receptor affinity.

Based upon the similar pharmacological profile of the compounds of this invention and the known anxiolytics and antidepressants referred to above, the compounds of this invention are characterized as anxiolytic/antidepressant agents useful in the treatment of depression and in alleviating anxiety which conditions are directly manifested or indirectly involved in problems such as sexual dysfunction, senile dementia, eating disorders, and the like. The weak binding potential for the D-2 dopamine receptor further categorizes the compounds of this invention as possessing a very low liability for extra-pyramidal side effects which are known to attend dopamine binding activity.

Hence, the compounds of this invention are anxiolytic-anti-depressant agents which may be administered to a patient in need thereof, either neat or with a conventional pharmaceutical carrier. The pharmaceutical carrier may be solid or liquid as suitable for oral or parenteral administeration.

A solid carrier can include one or more substances which may also act as flavoring agents, lubricants, solubilisers, suspending agents, fillers, glidants, compression aids, binders or tablet-disintegrating agents; it can also be an encapsulating material. In powders, the carrier is a finely divided solid which is in admixture with the finely divided active ingredients. In tablets, the active ingredient is mixed with a carrier having the necessary compression properties in suitable proportions and compacted in the shape and size desired. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

Liquid carriers are used in preparing solutions, suspensions, emulsions, syrups, elixirs and pressurized compositions. The active ingredient can be dissolved or suspended in a pharmaceutically acceptable liquid carrier such as water, an organic solvent, a mixture of both or pharmaceutically acceptable oils or fats. The liquid carrier can contain other suitable pharmaceutical additives such as solubilizers, emulsifiers, buffers, preservatives, sweeteners, flavoring agents, suspending agents, thickening agents, colors, viscosity, regulators, stabilizers or osmo-regulators. Suitable examples of liquid carriers for oral and parenteral administration include water (particularly containing additives as above, e.g. cellulose derivatives, preferably sodium carboxymethyl cellulose), alcohols (including monohydric alcohols and polyhydric alcohols, e.g., glycols) and their derivatives, and oils (e.g. fractionated coconut oil and arachis oil). For parenteral administration, the carrier can also be an oil ester such as ethyl oleate and isopropyl myristate. Sterile liquid carriers are used in sterile liquid form compositions for parenteral administration. The liquid carrier for pressurized compositions can be a halogenated hydrocarbon or other pharmaceutically acceptable propellant.

Liquid pharmaceutical compositions which are sterile solutions or suspensions can be utilized by, for example, intramuscular, intraperitoneal or subcutaneous injection. Sterile solutions can also be administered intravenously. Similarly, the compounds can be administered orally either in liquid or solid composition form.

Preferably, the pharmaceutical composition is in unit dosage form, e.g. as tablets or capsules. In such form, the composition is subdivided in unit dose containing appropriate quantities of the active ingredients; the unit dosage forms can be packaged compositions, for example packeted powders, vials, ampoules, prefilled syringes or sachets containing liquids. The unit dosage form can be, for example, a capsule or tablet itself, or it can be the appropriate number of any such compositions in package form.

The dosage to be used in the treatment of anxiety or depression must be subjectively determined by the attending physician. The variables involved included the specific state of depression or anxiety and the size, age and response pattern of the patient.

What is claimed is:

1. A compound of the formula:

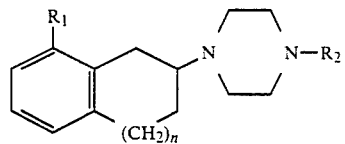

in which $R_1$ is hydroxy, alkoxy of 1 to 6 carbon atoms, amino, alkylamino of 1 to 6 carbon atoms, dialkylamino where each alkyl substituent has 1 to 6 carbon atoms, or alkanoylamino of 2 to 6 carbon atoms;

$R_2$ is 3-trifluoromethylphenyl, 3-halophenyl, 2-pyrimidinyl, mono halopyrimidin-2-yl, 2-pyrazinyl or mono halopyrazin-2-yl; and n is one of the integers 1 or 2;

or a pharmaceutically acceptable salt thereof.

2. A compound of claim 1 of the formula:

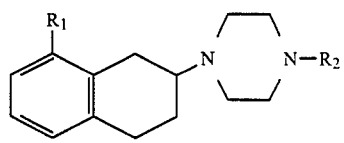

in which $R_1$ is hydroxy or methoxy;

$R_2$ is 3-trifluoromethylphenyl, 3-halophenyl or 2-pyrimidinyl;

or a pharmaceutically acceptable salt thereof.

3. The compound of claim 1 which is 1-(1,2,3,4-tetrahydro-8-methoxy-2-naphthalenyl)-4-[3-(trifluoromethyl)phenyl]piperazine or a pharmaceutically acceptable salt thereof.

4. The compound of claim 1 which is 2-[4-(1,2,3,4-tetrahydro-8-methoxy-2-naphthalenyl)-1-piperazinyl]-pyrimidine or a pharmaceutically acceptable salt thereof.

5. The compound of claim 1 which is 1-(1,2,3,4-tetrahydro-8-hydroxy-2-naphthalenyl-4-[3-(trifluoromethyl)phenyl]piperazine or a pharmaceutically acceptable salt thereof.

6. The compound of claim 1 which is 2-[4-(1,2,3,4-tetrahydro-8-hydroxy-2-naphthalenyl)-1-piperazinyl]-pyrimidine or a pharmaceutically acceptable salt thereof.

* * * * *